United States Patent [19]

Deasy, Jr.

[11] Patent Number: 5,171,211
[45] Date of Patent: Dec. 15, 1992

[54] METHOD OF BENEFICIALLY AFFECTING THE HUMAN BODY

[76] Inventor: John F. Deasy, Jr., 3731 S. Rosemary Way, Denver, Colo. 80237

[21] Appl. No.: 710,687

[22] Filed: Jun. 5, 1991

Related U.S. Application Data

[63] Continuation-in-part of Ser. No. 519,953.

[51] Int. Cl.$^5$ .......................... A61F 13/00; A61F 15/00
[52] U.S. Cl. .......................................... 602/61; 602/60; 602/62; 602/63; 128/856
[58] Field of Search ..................... 128/856; 602/60, 61, 602/62, 63

[56] References Cited

U.S. PATENT DOCUMENTS

| | | | |
|---|---|---|---|
| 1,823,178 | 9/1931 | Walton | 66/172 E |
| 3,097,644 | 7/1963 | Parker | 602/79 |
| 3,459,192 | 8/1969 | Thompson | 450/111 |
| 4,139,003 | 2/1979 | Little et al. | 602/3 |
| 4,926,851 | 5/1990 | Bulley | 602/60 |

*Primary Examiner*—Paul Prebilic
*Attorney, Agent, or Firm*—Gary M. Polumbus

[57] ABSTRACT

An elastic garment and method of using same are disclosed for providing therapeutic results as well as improved endurance and stamina. The garment includes six component parts which can be used in various combinations. Each component part is made of an elastic material so as to act in a compressive manner on the body part which it surrounds. A pant-like portion of the garment extends from the waist downwardly through two leg segments to a location beneath the knee joints. A pair of tubular leg portions extend from the feet upwardly beyond the knee joints so as to form an overlap with the leg sections of the pant-like portion. In a similar manner, a coat-like portion is worn around the upper torso or chest and includes depending sleeves which extend beyond the elbow joints. Tubular arm portions extend from the wrists upwardly beyond the elbow joint to form an overlap with the sleeves. Terminal edges of each component part have enlarged beads formed therein which act like garters in compressing the veins and arteries in the circulatory system. The method includes the steps of providing the various component parts and placing them on the body of a user in accordance with the manner in which the parts are adapted to be placed on the body.

9 Claims, 3 Drawing Sheets

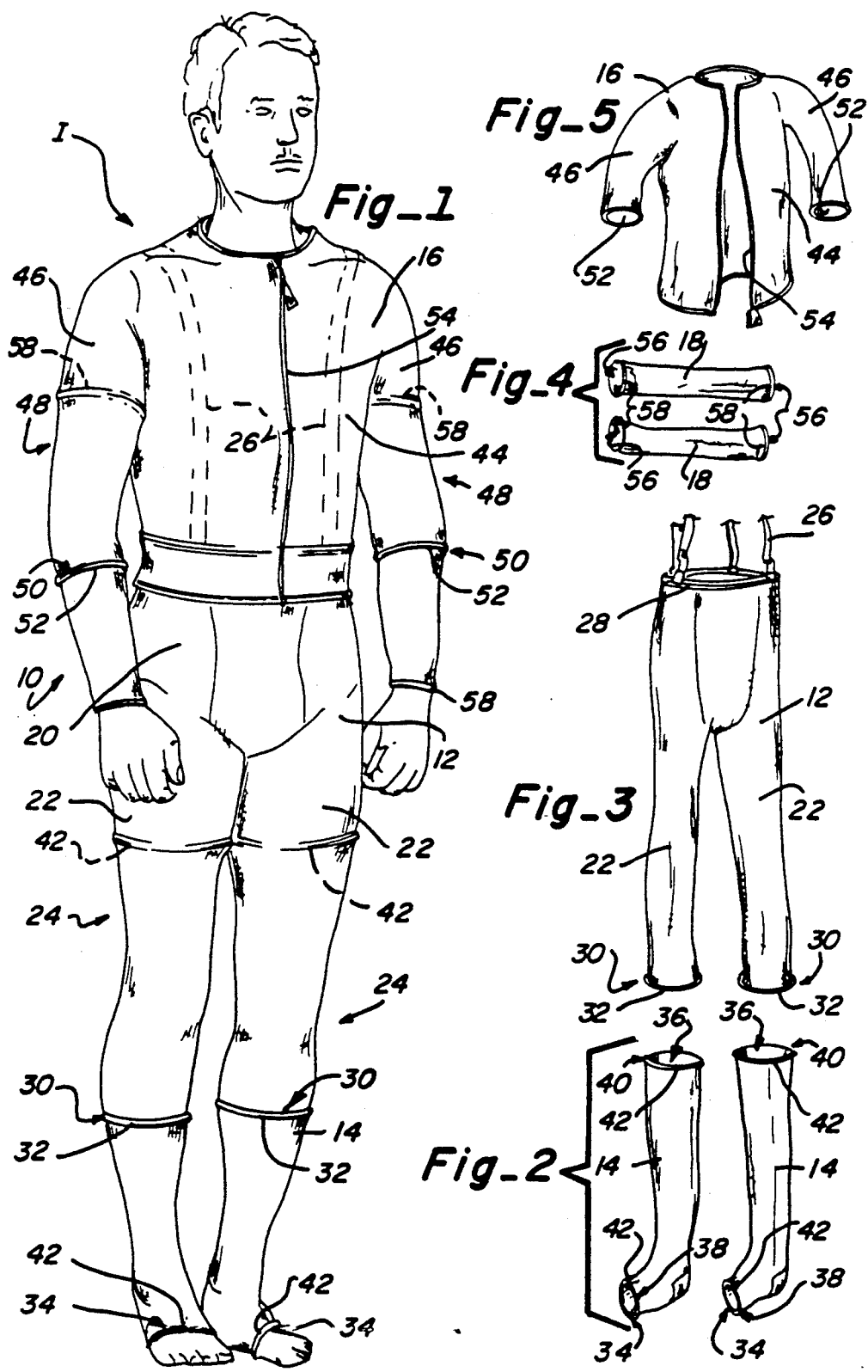

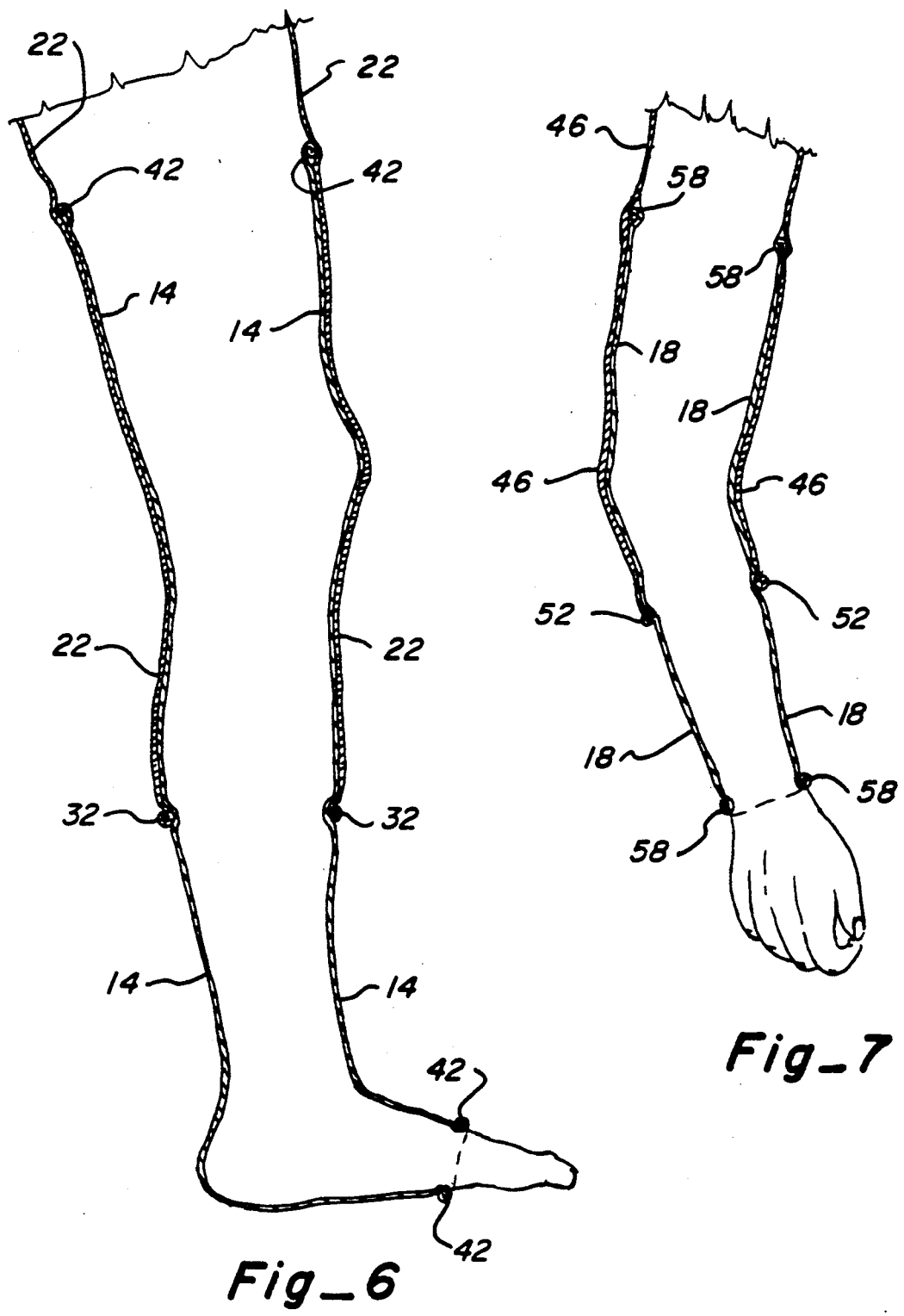

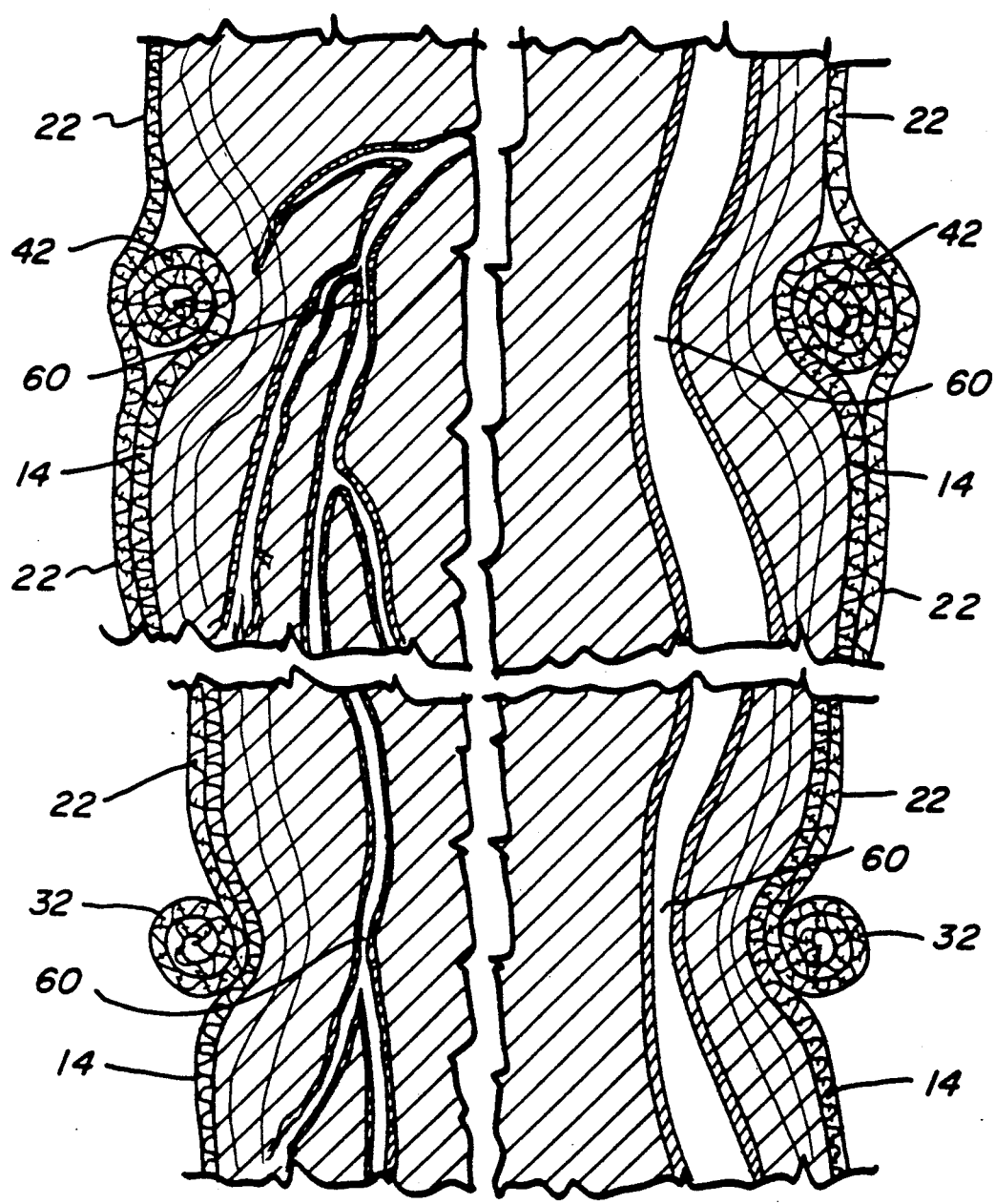
Fig_8

METHOD OF BENEFICIALLY AFFECTING THE HUMAN BODY

CROSS REFERENCE TO RELATED APPLICATIONS

This application is a continuation-in-part of my copending application Ser. No. 07/519,953 filed May 7, 1990 now abandoned for ELASTIC GARMENT.

BACKGROUND OF THE INVENTION

1. Field of the Invention

The present invention relates generally to articles of clothing and more particularly to an elastic garment which can be worn for therapeutic reasons or to improve one's endurance and stamina and to a method of using the garment to beneficially affect the human body.

2. Description of the Prior Art

Garments of various types have been used for many years to treat various body ailments or to provide comfort in response to bodily injury. Many of these garments are made of an elastic material and are adapted to surround or cover various body parts depending on the objective. An example of such a garment is shown in the old patent to Walter No. 824,456, issued Jun. 26, 1906, wherein a soft rubber garment is described as being capable of being worn next to the body whereby perspiration and heat are retained within the same for therapeutic purposes. The garment includes an upper portion worn as an undershirt and a lower portion referred to as drawers with the sleeves of the undershirt extending elbow length and the legs of the drawers extending knee length.

Another example of an elastic item is shown in the old patent to Lubin No. 366,590, issued Jul. 12, 1887, wherein elastic bandages are provided and can be worn around a midsection of the arm so as to surround the elbow joint, around an individual's abdominal area, or on the legs wherein the bandages extend from the feet up to a location that is approximately mid-thigh. The bandages are used to control varicose veins.

A surgical stocking is disclosed in U.S. Pat. No. 1,823,178 issued to O. H. Walton on Sep. 15, 1931 with the stocking being disclosed as being useful for supporting the lower leg of a user when such support is indicated for treating sprains or other lesions.

The patent to Omer J. Bowen No. 4,180,065 issued Dec. 25, 1979 discloses an anti-embolism stocking which is worn on the leg in order to control the blood supply of the vascular system in the leg. The stocking distributes a varied pressure along the length of the leg to inhibit the pooling of blood and forces the blood to move with an even distribution through the patient's leg.

More recently, applicant has become aware of an elastic garment that is similar to a tight pair of pants but which is made of a relatively heavy and extremely elastic fabric. The garment extends the full length of the legs and around the ankles so as to partially enclose the feet. The garment is manufactured by Truform of Cincinnati, Ohio, and is marketed under the brand name "Legotards" and carries Stock No. 797. The trouble with the Truform garment is that it is extremely difficult to get into and is similar to putting a girdle in that it extends from the waist to the feet. As a result, it has very severe limitations in use. By way of example, it is nearly impossible for a bedridden patient to put the garment on even though once the garment is on it has significant therapeutic value.

It was to overcome the limitations in the above-noted prior art devices and to provide an improved method for beneficially treating or affecting the human body that the present was made. It is also significant to note that applicant has observed unexpected results with the garment of the present invention and its method of use beyond those which would be expected from other elastic therapeutic devices of the type currently existing in the prior art.

SUMMARY OF THE INVENTION

The articles of the present invention consists of an elastic garment that includes several component parts enabling it to be easily put on and to be specifically directed toward therapeutic use in specific body locations. It has also been found to improve endurance and stamina apart from its therapeutic values and, accordingly, has beneficial uses beyond the medical field.

The garment includes portions that can be worn below the waist and/or above the waist. The portions which are worn below the waist include a pant-like portion which surrounds the hips of a user and extends downwardly from the waist through two leg segments to a location below the knee joints. Complementary tube-like leg portions extend from the feet upwardly to a location above the knee joint so as to form overlaps with the pant-like portion at the knee joint.

The upper portion may be characterized as including a coat-like portion that surrounds the user's chest and includes arm segments that extend beyond the elbow joints. Tube-like arm portions extend from the wrists upwardly beyond the elbow joints so as to form overlaps with the coat-like portion at the elbow joints.

Each component part of the garment includes an edge portion having an enlarged bead formed therein so that a bead exists above and below each elbow and knee joint establishing a garter-like effect.

It will be appreciated that the pant-like portion can be worn with or without the coat-like portion and can be used in combination with one or both of the tube-like leg portions depending upon the desired results from use of the garment. Similarly, the coat-like portion can be used with or without the pant-like portion and can be used with one or both of the tube-like arm portions again dependent upon the desired results from use of the garment.

The method of the present invention comprises the steps of providing an article or garment of the aforenoted type and wearing the article to beneficially treat or affect the body.

The garment has proven to be very effective in treating edema, and it is presumed that it would be equally effective in treating other bodily ailments such as varicose veins or the like. The garment has also been found by applicant to improve endurance and stamina irrespective of any medical purpose for which the garment might be worn.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 1 is a perspective view of an individual wearing each component part of the elastic garment of the present invention.

FIG. 2 is a perspective view of the tubular leg portions of the garment shown in FIG. 1.

FIG. 3 is a perspective view of the pant-like portion of the garment shown in FIG. 1.

FIG. 4 is a perspective view of the tubular arm portions of the garment shown in FIG. 1.

FIG. 5 is a perspective view of the coat-like portion of the garment shown in FIG. 1.

FIG. 6 is an enlarged fragmentary section taken through a leg of an individual illustrating the pant-like portion and one of the tubular leg portions in position on the leg.

FIG. 7 is a fragmentary section illustrating a portion of the coat-like portion and a tubular arm portion of the garment of the present invention in place on the arm of an individual user.

FIG. 8 is an enlarged fragmentary section taken through the leg of an individual illustrating the enlarged beads on the pant-like portion and one of the tubular leg portions as they engage the leg of a user above and below the knee joint.

DESCRIPTION OF THE PREFERRED EMBODIMENT

As can be seen in FIG. 1, the elastic garment 10 of the present invention includes six component parts which can be worn in various combinations depending upon the intended use. More particularly, the elastic garment of the present invention includes a pant-like portion 12 (FIG. 1 and 3), a pair of tubular leg portions 14 (FIGS. 1 and 2), a coat-like portion 16 (FIGS. 1 and 5) and a pair of tubular arm portions 18 (FIGS. 1 and 4). Each component part is made of a flexible relatively heavy and strong elastic material with an example of an acceptable material being the type utilized by Truform of Cincinnati, Ohio, in the manufacture of a product marketed under the brand name "Legotard" and identified by Stock No. 797.

The pant-like portion 12 includes an upper abdominal segment 20 that extends around the waist and downwardly therefrom to a pair of integral leg segments 22 which are adapted to extend past the knee joint 24 of an individual wearing the garment. While not forming a part of the pant-like portion, a pair of suspenders 26 are illustrated in FIG. 3 and may be useful in holding the garment in a desired position on the user in a conventional manner. As is conventional with many elastic garments, the waist 28 may be provided with a reinforced area which is formed by overlapping the material and hemming the overlap to establish a double thickness band at the waist location. The lower terminal edges 30 of the leg segments 22 include an enlarged bead 32 extending therearound which in the disclosed embodiment is formed merely by rolling the edge over itself several times. The purpose for the bead will become more clear later.

The tubular leg portions 14 are identical and consist of elongated tube-like segments having a right angle formed near the lower end thereof and having openings 34 and 36 at each end. When worn, the foot of the user projects out of the opening 34 at the lower end of the associated leg portion so that a circular edge 38 of the leg portion surrounds the foot at approximately a midpoint along the length of the foot. Both the circular edge 38 at the lower end of the leg portion and a similar edge 40 at the upper end of the leg portion include an enlarged bead 42 which again may be formed by rolling the edge over itself several times. The length of the leg portions 14 is such that the upper edge 40 surround the user's leg at a location above the knee joint 24 so as to form an overlap with the leg segments 22 of the pant-like portion at the knee joint when both are worn by an individual.

The coat-like portion 16 as illustrated in FIG. 5 includes a main body portion 44 that is adapted to surround the chest or the main torso of a user and includes a pair of integral sleeves 46 which are adapted to extend beyond or below the elbow joints 48 of a user. The terminal end of the sleeves define an edge 50 having an enlarged bead 52 which again in the preferred embodiment is formed merely by rolling the edge over itself several times. A zipper 54 is provided up the front of the coat-like portion to permit the coat-like portion to be easily taken on and off but when in use with the zipper closed, the garment provides a tight compressive fit over the chest of the user.

The tubular arm portions 18 as illustrated in FIG. 4 are relatively straight tubular segments having circular edges 56 at opposite ends with each edge having an enlarged bead 58 formed therein. As with the previously described edges of the elastic garment, the bead in the preferred embodiment is formed merely by rolling the edge over itself several times. The length of the tubular arm portions 18 is such as to extend from the wrist of a user up beyond the elbow joint 48 so as to form an overlap with the sleeves 46 of the coat-like portion.

As can be appreciated from FIGS. 1, 6 and 7, after the tubular leg and arm portions have been placed on the calves and forearms of the user respectively so as to extend beyond the knee joints and elbow joints respectively, the pant-like portion 12 and coat-like portion 16 are put on so that the leg segments 22 of the pant-like portion extend up and over the tubular leg portions 14 so as to overlap the tubular leg portions at the knee joint 24. Likewise, the sleeves 46 of the coat-like portion are pulled up over the tubular arm portions 18 so as to overlie the tubular arm portions at the elbow joints 48.

As mentioned previously, each component part or portion of the garment is made of an elastic material and is sized so as to be compressive on the body of a user. The enlarged beads along the edges of the components actually compress the body more than the remaining portions of the components and in effect act like a garter in compressing the body part of the user immediately beneath the bead.

The method of the present invention comprises the steps of providing a garment as described hereinabove and wearing the garment to beneficially treat or affect the body.

While applicant is not sure as to why the garment performs in the manner in which it does to beneficially affect the body, it has been found to be highly effective in reducing edema and providing improved endurance and stamina when in use. While one would expect an improvement in a condition of edema through use of a compressive garment, applicant feels the garment 10 has gone beyond expected results in reducing the symptoms of edema and has also increased the user's stamina.

With reference to FIG. 8, wherein the suspected effect of the garment on the veins and/or arteries 60 of a user is illustrated, it will be seen that the garment, particularly along the enlarged beaded edges thereof, compresses the veins and/or arteries therebeneath thereby effecting the flow of blood through the veins and arteries. For whatever reason, the effect of the garment on the circulatory system is felt to have a bearing on the therapeutic and other qualities of the garment with the results being felt by applicant to be superior to those available with prior art garments. In addition, the garment is relatively easy to put on and take off due to the fact that the portions of the garment covering the arms and legs are in segments rather than in one continuous part as with the Legotard garment told by Truform of Cincinnati, Ohio. In addition to the relative ease with which the garment can be put on and off, it is felt that the garter effect at locations above and below both the knee joints and the elbow joints provides anatomical reactions which improve the therapeutic and other benefits of the garment. It is also possible to only use selected parts of the garment where necessary. For example, if one were treating varicose veins in the left leg, it might be desired to wear only the pant-like portion 12 and the left tubular leg portion 14. Other combinations will be apparent depending upon specific objectives.

Although the present invention has been described with a certain degree of particularity, it is understood that the present disclosure had been made by way of example, and changes in detail or structure may be made without departing from the spirit of the invention, as defined in the appended claims.

I claim:

1. A method of beneficially affecting the human body comprising the steps of providing an elastic garment having at least two component parts, one of said component parts being adapted to surround a portion of a user's body immediately above and across a joint in the body, and the other component part being adapted to surround a portion of a user's body immediately below and across said joint whereby the component parts are adapted to overlap only at said joint, and placing the component parts on the user's body in accordance with the manner in which the parts are adapted to be placed on the body.

2. The method of claim 1 further including the steps of providing at least one enlarged edge on each component part with the edges having a bead formed therein such that an enlarged edge will be disposed above and below said joint when the parts are placed on the user's body, said enlarged edges having a greater compressive effect on the user's body than the remaining portions of the garment and, constricting the flow of blood beneath the enlarged edges via the greater compressive effect provided by said enlarged edges.

3. The method of claim 1, further including the step of surrounding the user's hips with said one component part and wherein said one component part includes leg portions adapted to extend slightly below the knee joints of the user.

4. The method of claim 3, further including the step of surrounding at least one of the calves of the user with the other component part and extending the other component part above the knee joint to form an overlap with said one component part at the knee joint.

5. The method of claim 4, further including the steps of providing two of said other component parts, placing each of said other component parts on the calves of the user and extending each of the two other component parts above the associated knees of the user.

6. The method of claim 2, further including the step of forming the enlarged edges on the component parts by rolling the edges of the material from which the component parts are made.

7. The method of claim 2, further including the steps of extending said one component part around the user's chest and wherein said one component part includes arm portions, and extending the arm portions slightly beyond the elbow joints of the user.

8. The method of claim 2, further including the steps of placing said other component part on the user so as to surround a forearm of the user and extending the other component part above the associated elbow joint to form an overlap with the said one component part at the elbow joint.

9. The method of claim 8, wherein there are two of said other component parts and further including the steps of placing each of said other component parts on the user's forearm and extending said other component parts above the associated elbow joints.

* * * * *